United States Patent [19]

Yamada et al.

[11] Patent Number: 4,544,268
[45] Date of Patent: Oct. 1, 1985

[54] METHOD AND APPARATUS FOR DETECTING FLAW ON THREADS OF MALE SCREW

[75] Inventors: Takeo Yamada; Mitsuaki Uesugi, both of Yokohama; Masaru Okamura, Kawasaki, all of Japan

[73] Assignee: Nippon Kokan Kabushiki Kaisha, Tokyo, Japan

[21] Appl. No.: 567,949

[22] Filed: Jan. 4, 1984

[30] Foreign Application Priority Data

Jan. 31, 1983 [JP] Japan .................................. 58-12952

[51] Int. Cl.$^4$ ...................... G01B 11/24; G01B 11/30
[52] U.S. Cl. .................................... 356/394; 356/398; 356/237
[58] Field of Search ................. 356/376, 394, 398, 237

[56] References Cited
FOREIGN PATENT DOCUMENTS 54-50163  5/1978  Japan .
2115924   9/1983  United Kingdom .

Primary Examiner—R. A. Rosenberger
Assistant Examiner—Michael Vollero
Attorney, Agent, or Firm—Frishauf, Holtz, Goodman & Woodward

[57] ABSTRACT

A method and an apparatus for detecting a flaw on threads of a male screw, which comprises: fully applying a light from a light source onto tops, roots and flanks of threads of a male screw while rotating the male screw around the axis thereof; continuously measuring, by means of a photoelectric converter, electric signal values corresponding to variations in brightness of the male screw in the axial direction thereof during one turn of the male screw around the axis thereof; moving-averaging the thus measured electric signal values corresponding to the variations in brightness of the male screw in the axial direction thereof; determining electric signal values corresponding to variations in brightness of the male screw in the circumferential direction thereof, on the basis of the thus moving-averaged electric signal values corresponding to the variations in brightness of the male screw in the axial direction thereof; obtaining a mean square value of the thus determined electric signal values corresponding to the variations in brightness of the male screw in the circumferential direction thereof; and comparing the thus obtained mean square value with a previously set reference value to detect a flaw on the threads of the male screw.

4 Claims, 14 Drawing Figures

FIG. 6(C')
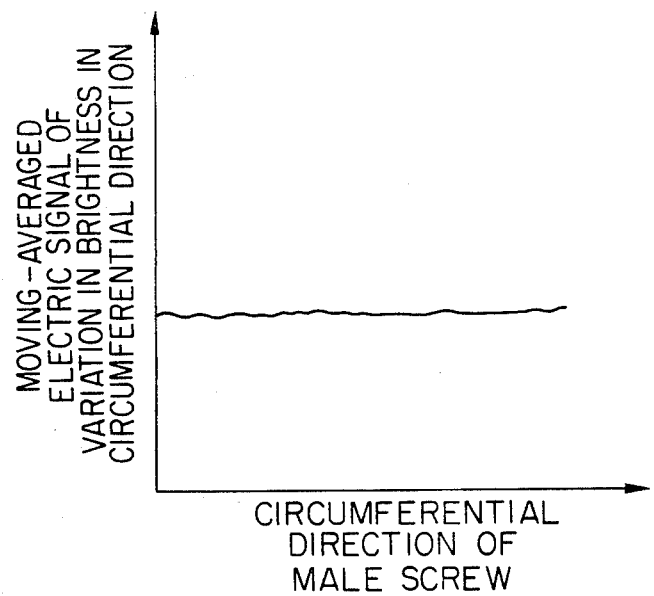
FIG. 6(D')
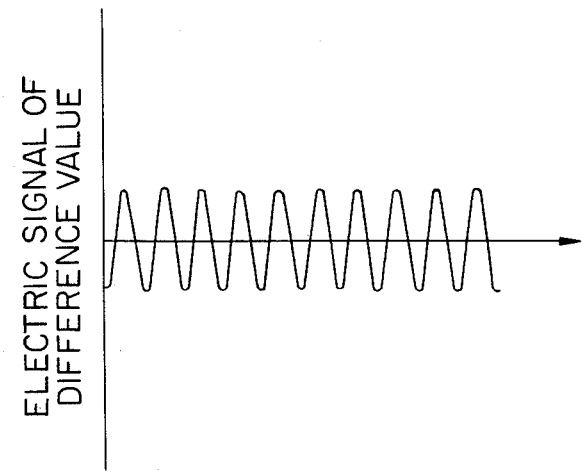

METHOD AND APPARATUS FOR DETECTING FLAW ON THREADS OF MALE SCREW

REFERENCE TO PATENTS, APPLICATIONS AND PUBLICATIONS PERTINENT TO THE INVENTION

Japanese Patent Provisional Publication No. 54-150,163, discussed hereafter under the heading "BACKGROUND OF THE INVENTION".

FIELD OF THE INVENTION

The present invention relates to a method and an apparatus for accurately detecting a flaw on threads of a male screw.

BACKGROUND OF THE INVENTION

For example, when cutting threads of a male screw made of a pipe with a cutting tool, chattering of the tool may cause flaws such as chattering flaws on the threads. It has conventionally been the usual practice to depend on an operator's visual inspection for the detection of these flaws on threads of a male screw, and this has involved the following problems:

(1) It is difficult to ensure certain detection of flaws on threads.
(2) Visual inspection requires a high degree of attention, resulting in considerable fatigue of the operator.
(3) The detecting operation requires a long time and is not therefore efficient.

As an apparatus for solving the above-mentioned problems and accurately detecting a flaw on threads of a male screw, the following apparatus for detecting a flaw on threads of a male screw is disclosed in Japanese Patent Provisional Publication No. 54-150,163 dated Nov. 26, 1979, which comprises:

a rotating means for rotating a male screw at a prescribed circumferential speed around the axis thereof; a light source for uniformly applying a light onto substantially the entire surface of threads of said male screw in the axial direction thereof and at least part of the surface of said threads of said male screw in the circumferential direction thereof, said light source being provided at such a position that the optical axis obliquely intersects the axis of said male screw so that said light from said light source is not applied onto roots of said threads of said male screw; a photoelectric converter for continuously measuring, during one turn of said male screw around the axis thereof, a brightness distribution of said male screw corresponding to tops of said threads of said male screw in the axial direction thereof onto which said light from said light source is applied; and an information processing means for continuously comparing, during said one turn of said male screw, said brightness distribution of said male screw as measured by said photoelectric converter with a previously set reference brightness distribution, to detect a flaw on said threads of said male screw (hereinafter referred to as the "prior art").

However, the above-mentioned prior art, in which a flaw on threads of a male screw is detected by the inconsistency between the reference brightness distribution and the brightness distribution of the male screw in the axial direction thereof as measured by the photoelectric converter, which occurs when the light from the light source is applied onto the roots of the threads, involves the following problems:

(1) Unless the light from the light source is applied onto the roots of the threads, it is impossible to detect a flaw on the tops, the roots and the flanks of the threads of the male screw, if any.
(2) Even threads with no flaws may be erroneously judged as having flaws because of dirt or dust depositing on the tops of the threads.

Under such circumstances, there is a strong demand for a method and an apparatus for ensuring rapid detection of flaws such as chattering flaws produced on tops, roots and flanks of threads of a male screw, but such a method and an apparatus have not been proposed as yet.

SUMMARY OF THE INVENTION

An object of the present invention is therefore to provide a method and an apparatus which ensure rapid detection of flaws such as chattering flaws produced on tops, roots and flanks of threads of a male screw.

In accordance with one of the features of the present invention, there is provided a method for detecting a flaw on threads of a male screw, which comprises:

uniformly applying a light onto substantially the entire surface of threads of a male screw in the axial direction thereof and at least part of the surface of said threads of said male screw in the circumferential direction thereof while rotating said male screw at a prescribed circumferential speed around the axis thereof;

continuously measuring, during one turn of said male screw around the axis thereof, electric signal values corresponding to variations in brightness of the surface of said male screw in the axial direction thereof, which are caused by tops, roots and flanks of said threads of said male screw onto which said light is applied;

obtaining an average value of the thus measured electric signal values corresponding to said variations in brightness of said male screw in the axial direction thereof; and comparing the thus obtained average value of said electric signal values with a previously set reference value, to detect a flaw on said threads of said male screw;

characterized by:

fully applying said light onto the tops, the roots and the flanks of said threads of said male screw; and said obtaining step of said average value of said electric signal values comprises:

(1) moving-averaging, during said one turn of said male screw, said electric signal values corresponding to said variations in brightness of said male screw in the axial direction thereof;
(2) continuously determining, during said one turn of said male screw, electric signal values corresponding to variations in brightness of said male screw in the circumferential direction thereof, on the basis of the thus moving-averaged electric signal values corresponding to said variations in brightness of said male screw in the axial direction thereof; and
(3) obtaining a mean square value from the thus determined electric signal values corresponding to said variations in brightness of said male screw in the circumferential direction thereof, thereby using the thus obtained mean square value of said electric signal values as said average value of said electric signal values to compare said mean square value of said electric signal values with said previously set reference value to detect a flaw on said threads of said male screw.

BRIEF DESCRIPTION OF THE DRAWINGS

FIG. 6(A') is a descriptive view illustrating, in the form developed in the circumferential direction of a male screw having threads with flaws, electric signal values corresponding to variations in brightness of the male screw in the axial direction thereof, as moving-averaged during one turn of the male screw in accordance with the method of the present invention;

DETAILED DESCRIPTION OF PREFERRED EMBODIMENTS

From the above-mentioned point of view, extensive studies were carried out to develop a method and an apparatus which ensure rapid detection of flaws such as chattering flaws produced on tops, roots and flanks of threads of a male screw. As a result, the following finding was obtained: it is possible to ensure rapid detection of a flaw produced on tops, roots and flanks of threads of a male screw by fully applying a light from a light source onto the tops, the roots and the flanks of the threads of the male screw while rotating the male screw at a prescribed circumferential speed around the axis thereof; moving-averaging, during one turn of the male screw around the axis thereof, electric signal values corresponding to variations in brightness of the male screw in the axial direction thereof; continuously determining, during the one turn of the male screw, electric signal values corresponding to variations in brightness of the male screw in the circumferential direction thereof, on the basis of the thus moving-averaged electric signal values corresponding to the variations in brightness of the male screw in the axial direction thereof; obtaining a mean square value from the thus obtained electric signal values corresponding to the variations in brightness of the male screw in the circumferential direction thereof; and comparing the thus obtained mean square value with a previously set reference value.

The present invention was made on the basis of the above-mentioned finding. The method and the apparatus for detecting a flaw on threads of a male screw are described below with reference to the drawings.

Figure 1:
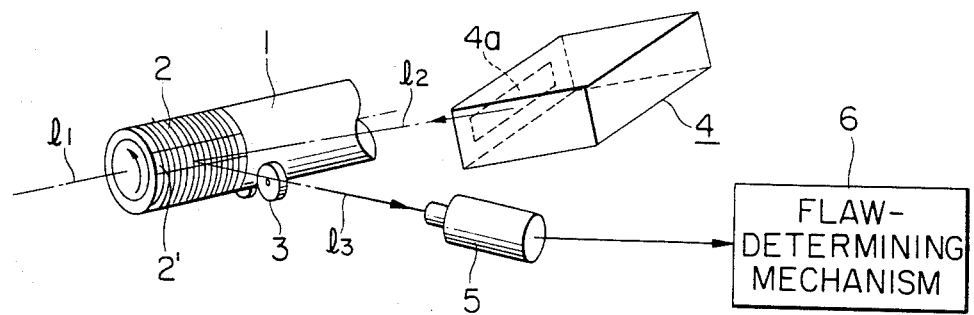
FIG. 1 is a schematic descriptive perspective view illustrating an embodiment of the apparatus of the present invention.

FIG. 1 is a schematic descriptive perspective view illustrating an embodiment of the apparatus of the present invention. As shown in FIG. 1, a male screw 1 made of a pipe having threads 2 cut at an end portion thereof is horizontally placed on a male screw rotating means 3, and is rotated by the male screw rotating means 3 at a prescribed circumferential speed around the axis thereof. A light source 4 is provided at a prescribed distance from the male screw 1 at a position from which a light from the light source 4 is fully applied onto tops, roots and flanks of the threads 2 of the male screw 1. The light source 4 has a slit 4a through which the light is applied onto substantially the entire surface of the threads 2 of the male screw 1 in the axial direction thereof and at least part of the surface of the threads 2 of the male screw 1 in the circumferential direction thereof. In the embodiment shown in FIG. 1, the light source 4 is provided at a position that the optical axis $l_2$ thereof intersects the axis $l_1$ of the male screw 1 substantially at right angles.

A photoelectric converter 5 is provided at a prescribed distance from the male screw 1 at such a position as to permit measurement of variations in brightness of a portion 2' of the surface of the male screw 1 onto which the light from the light source 4 is applied. The photoelectric converter 5 continuously measures, during one turn of the male screw 1 around the axis thereof, electric signal values of voltage or current corresponding to variations in brightness of the surface of the male screw 1 in the axial direction thereof, which are caused by the tops, the roots and the flanks of the threads 2 of the male screw 1 in the portion 2' onto which the light from the light source 4 is applied. In the embodiment shown in FIG. 1, the photoelectric converter 5 is provided near the light source 4 at a position that the optical axis $l_3$ of the photoelectric converter 5 intersects the axis $l_1$ of the male screw 1 substantially at right angles.

In FIG. 1, 6 is a flaw-determining mechanism for comparing an average value of the electric signal values corresponding to the variations in brightness of the male screw 1 in the axial direction thereof, as measured by the photoelectric converter 5, with a previously set reference value, to detect a flaw on the threads 2 of the male screw 1. The flaw-determining mechanism 6 comprises a memory 11 for continuously storing, during the one turn of the male screw 1, the electric signal values corresponding to the variations in brightness of the male screw 1 in the axial direction thereof, as measured by the photoelectric converter 5; and a flaw-detecting means for obtaining an average value of the electric signal values corresponding to the variations in brightness of the male screw 1 in the axial direction thereof, as continuously stored in the memory 11 during the one turn of the male screw 1, and for comparing the thus obtained average value of the electric signal values, with the previously set reference value, to detect a flaw on the threads 2 of the male screw 1.

As shown in FIG. 1, the light is fully applied onto the tops, the roots and the flanks of the threads 2 of the male screw 1 from the light source 4 provided at a position that the optical axis $l_2$ thereof intersects the axis $l_1$ of the male screw 1, substantially at right angles, while rotating the male screw 1 by the male screw rotating means 3 at a prescribed circumferential speed. As mentioned above, the photoelectric converter 5 continuously measures, during the one turn of the male screw 1, the electric signal values corresponding to the variations in brightness of the male screw 1 in the axial direction thereof, which are caused by the tops, the roots and the flanks of the threads 2 of the male screw 1 in the portion 2' onto which the light from the light source 4 is applied.

Figure 2A:
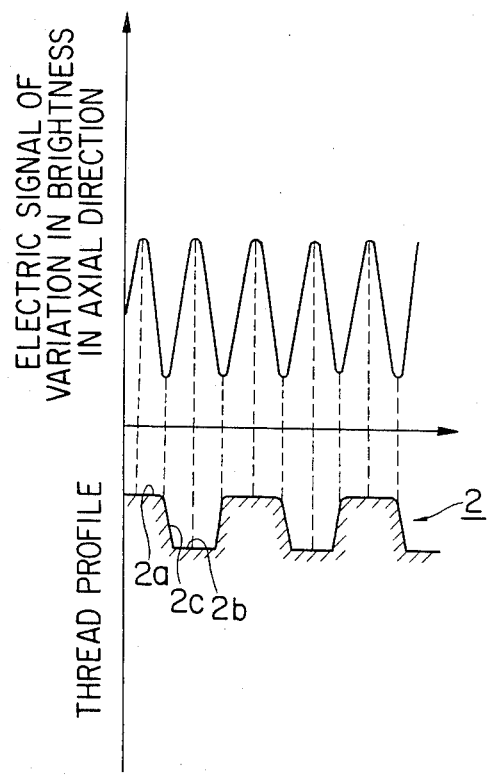
FIG. 2(A) is a descriptive view illustrating electric signal values corresponding to variations in brightness of a male screw having threads with no flaws in the axial direction thereof and the profile of the male screw, when measuring the male screw by a photoelectric converter in accordance with the method of the present invention.
Figure 2B:
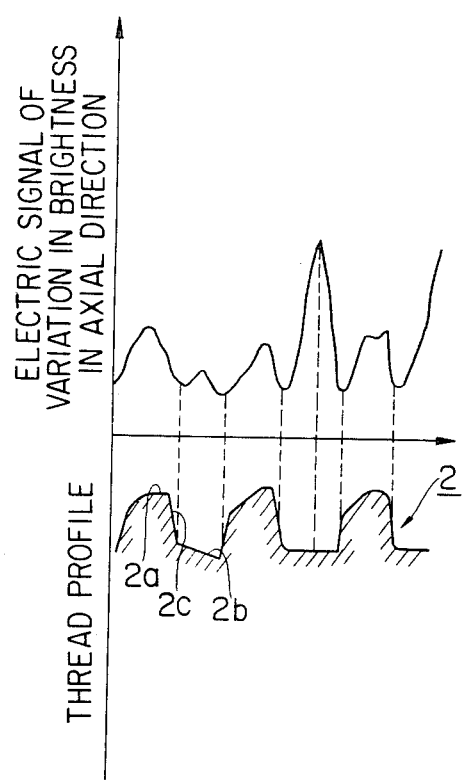
FIG. 2(B) is a descriptive view illustrating electric signal values corresponding to variations in brightness of a male screw having threads with flaws in the axial direction thereof and the profile of the male screw, when measuring the male screw by a photoelectric converter in accordance with the method of the present invention.

FIG. 2(A) is a descriptive view illustrating electric signal values corresponding to variations in brightness of a male screw having threads with no flaws in the axial direction thereof and the profile of the male screw, when measuring the male screw by a photoelectric converter in accordance with the method of the present invention, and FIG. 2(B) is a descriptive view illustrating electric signal values corresponding to variations in brightness of a male screw having threads with chattering flaws in the axial direction thereof and the profile of the male screw, when measuring the male screw by a photoelectric converter in accordance with the method of the present invention. As shown in FIG. 2(A), brightness of the tops $2a$ and the roots $2b$ of the threads 2 with no flaws of the male screw 1 is high, and therefore electric signal values corresponding this brightness are also high, and the flanks $2c$ of the threads 2 of the male screw 1 have low brightness and hence low electric signal values corresponding thereto. Therefore, the electric signal values corresponding to the variations in brightness of the threads 2 with no flaws of the male screw 1 in the axial direction thereof repeat a uniform cycle of high and low values at a constant pitch. As shown in FIG. 2(B), in contrast, brightness of the tops $2a$ and the roots $2b$ of the threads 2 with flaws of the male screw 1 is lower than that of the tops $2a$ and the roots $2b$ of the threads 2 with no flaws and varies, and therefore, the electric signal values corresponding to this brightness are also lower than in the case of the threads with no flaws and vary. Therefore, the electric signal values corresponding to the variations in brightness of the threads 2 with flaws of the male screw 1 in the axial direction thereof show non-uniform variations and vary considerably.

Figure 3:
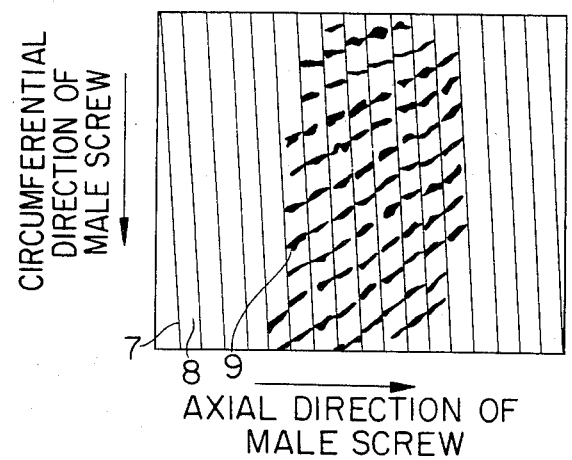
FIG. 3 is a descriptive view illustrating, in the form developed in the circumferential direction of a male screw having threads with flaws, electric signal values corresponding to variations in brightness of the male screw in the axial direction thereof, as measured by a photoelectric converter during one turn of the male screw in accordance with the method of the present invention.

FIG. 3 is a descriptive view illustrating, in the form developed in the circumferential direction of a male screw having threads with chattering flaws, electric signal values corresponding to variations in brightness of the male screw in the axial direction thereof, as measured by a photoelectric converter during one turn of the male screw in accordance with the method of the present invention. As shown in FIG. 3, the tops $2a$ and the roots $2b$ of the threads 2 with no flaws of the male screw 1 appear as bright portions 8 because of the high brightness, and the flanks $2c$ of the threads 2 of the male screw 1 appear as dark portions 7 because of the low brightness. Chattering flaws, if any, being produced on the tops $2a$ and the roots $2b$ of the threads 2 at intervals in the circumferential direction of the male screw 1, appear as dark portions 9 at intervals in the bright portions 8 representing the tops $2a$ and the roots $2b$ of the threads 2.

An average value of the electric signal values corresponding to the variations in brightness of the male screw 1 in the axial direction thereof, as continuously measured by the photoelectric converter 5, is compared with a previously set reference value in the flaw-determining mechanism 6 as mentioned below, to detect a flaw on the threads 2 of the male screw 1.

Figure 5:
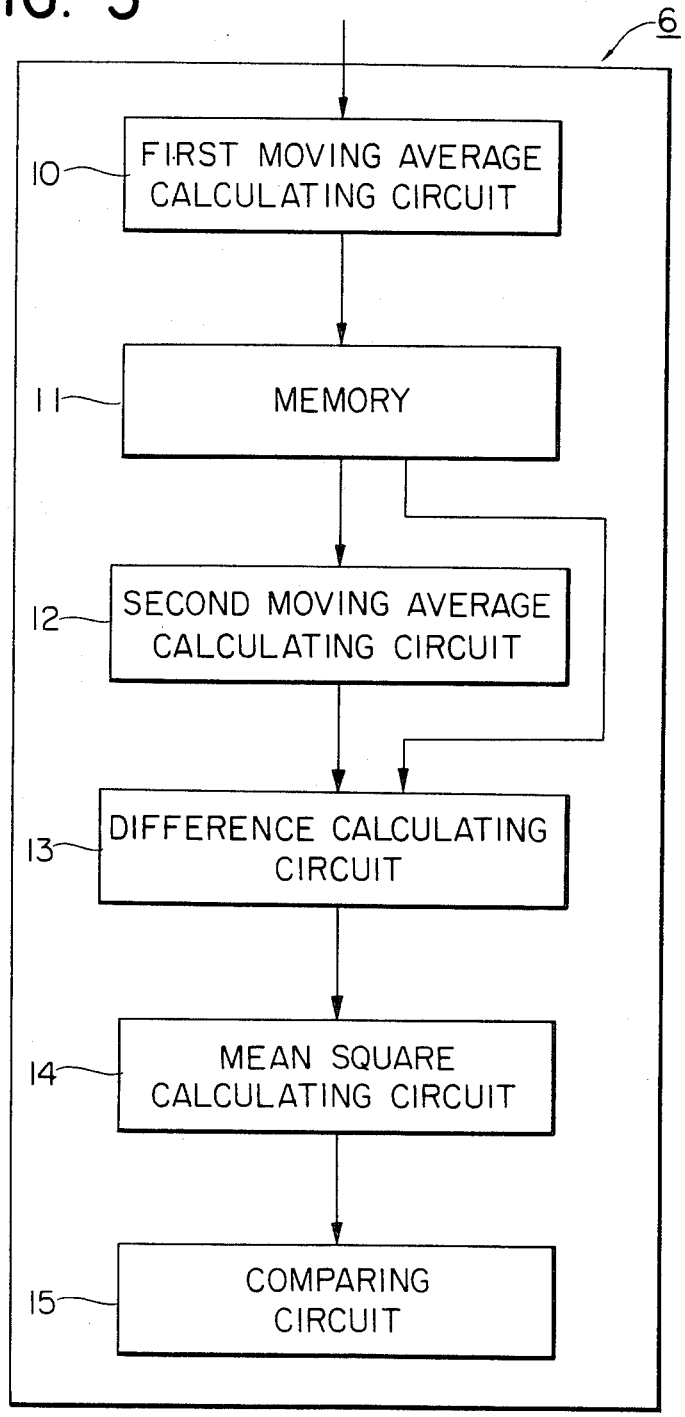
FIG. 5 is a circuit diagram illustrating an embodiment of the flaw-determining mechanism which is one of the components of the apparatus of the present invention.

FIG. 5 is a circuit diagram illustrating an embodiment of the flaw-determining mechanism 6. As shown in FIG. 5, the flaw-determining mechanism 6 comprises a memory 11 and a flaw-detecting means comprising a first moving average calculating circuit 10, a second moving average calculating circuit 12, a difference calculating circuit 13, a mean square calculating circuit 14 and a comparing circuit 15. The memory 11 includes a means for continuously determining, during the one turn of the male screw 1, electric signal values corresponding to variations in brightness of the male screw 1 in the circumferential direction thereof, on the basis of the electric signal values corresponding to the variations in brightness of the male screw 1 in the axial direction thereof, as measured by the photoelectric converter 5. The first moving average calculating circuit 10 is connected to both the photoelectric converter 5 and the memory 11. The second moving average calculating circuit 12, the difference calculating circuit 13, the mean square calculating circuit 14 and the comparing circuit 15 are connected to the memory 11 in this order.

The electric signal values corresponding to the variations in brightness of the male screw 1 in the axial direction thereof, as measured by the photoelectric converter 5 during the one turn of the male screw 1, are moving-averaged by the first moving average calculating circuit 10. As a result, the electric signal values corresponding to the variations in brightness shown by alternate appearance of the bright portions 8 representing the tops 2a and the roots 2b of the threads 2 and the dark portions 7 representing the flanks 2c of the threads 2 in the axial direction of the male screw 1 as shown in FIG. 3 are smoothed.

Figure 4:
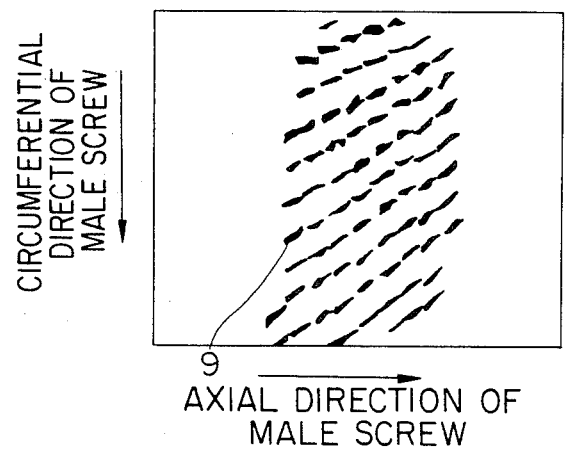
FIG. 4 is a descriptive view illustrating, in the form developed in the circumferential direction of a male screw having threads with flaws, electric signal values corresponding to variations in brightness of the male screw in the axial direction thereof, as moving-averaged during one turn of the male screw in accordance with the method of the present invention.

FIG. 4 is a descriptive view illustrating, in the form developed in the circumferential direction of a male screw having threads with flaws, electric signal values corresponding to variations in brightness of the male screw in the axial direction thereof, which are caused by the tops, the roots and the flanks of the threads of the male screw, as moving-averaged during one turn of the male screw in accordance with the method of the present invention as mentioned above. As shown in FIG. 4, the electric signal values corresponding to the variations in brightness shown by alternate appearance of the bright portions 8 representing the tops 2a and the roots 2b of the threads 2 and the dark portions 7 representing the flanks 2c of the threads 2 in the axial direction of the male screw 1 are smoothed, and only the dark portions 9 corresponding to chattering flaws become apparent.

The electric signal values corresponding to the variations in brightness of the male screw 1 in the axial direction thereof, as moving-averaged by the first moving average calculating circuit 10 are continuously stored by the memory 11 during the one turn of the male screw 1. Electric signal values corresponding to variations in brightness in the circumferential direction of the male screw 1 at a prescribed position are continuously determined by the memory 11. The above-mentioned prescribed position can be arbitrarily selected by the memory 11.

The electric signal values corresponding to the variations in brightness of the male screw 1 in the circumferential direction thereof, as determined by the memory 11, are entered in parallel into the second moving average calculating circuit 12 and the difference calculating circuit 13. The second moving average calculating circuit 12 moving-averages the electric signal values corresponding to the variations in brightness of the male screw 1 in the circumferential direction thereof produced by flaws such as chattering flaws to smooth same. The thus moving-averaged and smoothed electric signal values corresponding to the variations in brightness of the male screw 1 in the circumferential direction thereof are entered into the difference calculating circuit 13. The difference calculating circuit 13 calculates values of differences between the electric signal values corresponding to the variations in brightness of the male screw 1 in the circumferential direction thereof, as moving-averaged by the second moving average calculating circuit 12, on one hand, and the electric signal values before the moving-averaging corresponding to the variations in brightness of the male screw 1 in the circumferential direction thereof, as determined by the memory 11. The thus determined values of differences are entered into the mean square calculating circuit 14. The mean square calculating circuit 14 obtains a mean square value from the values of differences determined by the difference calculating circuit 13. The thus obtained mean square value is entered into the comparing circuit 15. The comparing circuit 15 compares the mean square value obtained by the mean square calculating circuit 14 with a previously set reference value, to detect a flaw on the threads 2 of the male screw 1.

Figure 6A:
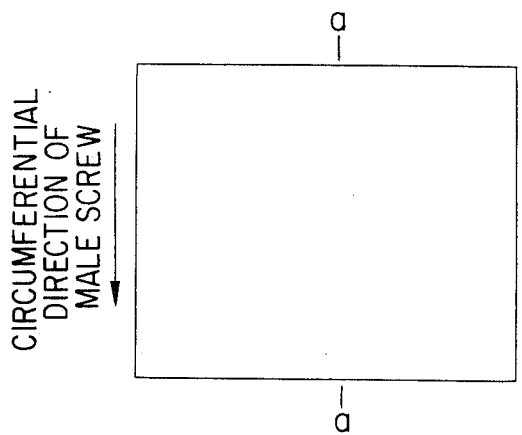
FIG. 6(A) is a descriptive view illustrating, in the form developed in the circumferential direction of a male screw having threads with no flaws, electric signal values corresponding to variations in brightness of the male screw in the axial direction thereof, as moving-averaged during one turn of the male screw in accordance with the method of the present invention.
Figure 6B:
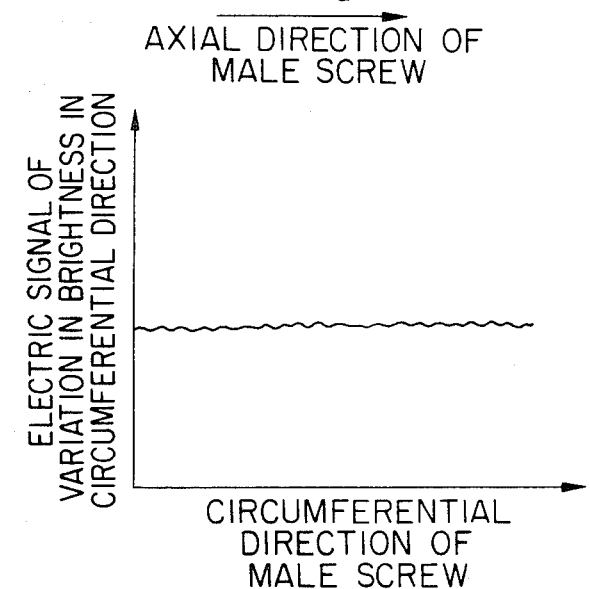
FIG. 6(B) is a graph illustrating electric signal values in the circumferential direction of the male screw, at the position of the line a—a in FIG. 6(A), as determined in accordance with the method of the present invention.
Figure 6C:
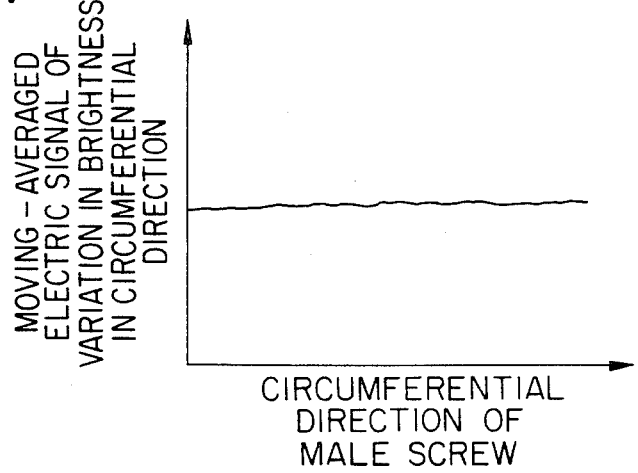
FIG. 6(C) is a graph illustrating electric signal values determined by moving-averaging the electric signal values in the circumferential direction of the male screw as shown in FIG. 6(B) in accordance with the method of the present invention.
Figure 6D:
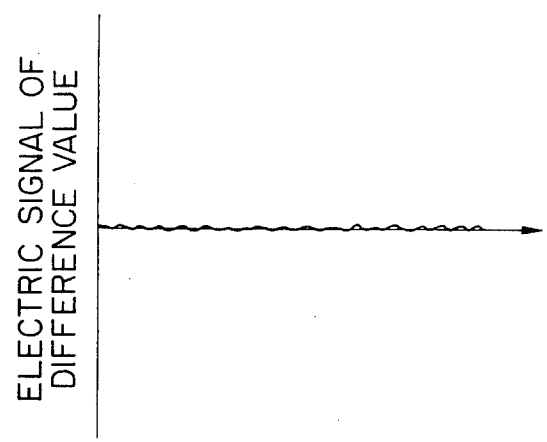
FIG. 6(D) is a graph illustrating values of differences between the electric signal values in the circumferential direction of the male screw before the moving-averaging as shown in FIG. 6(B), on one hand, and the electric signal values in the circumferential direction of the male screw after the moving-averaging as shown in FIG. 6(C), on the other hand, as determined in accordance with the method of the present invention.
Figure 6D:
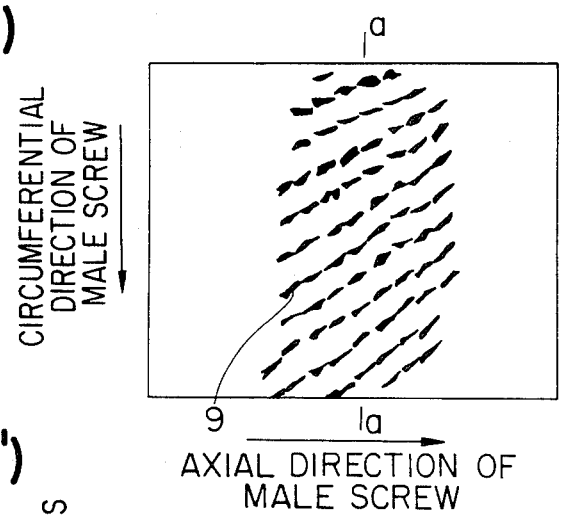
Figure 6D:
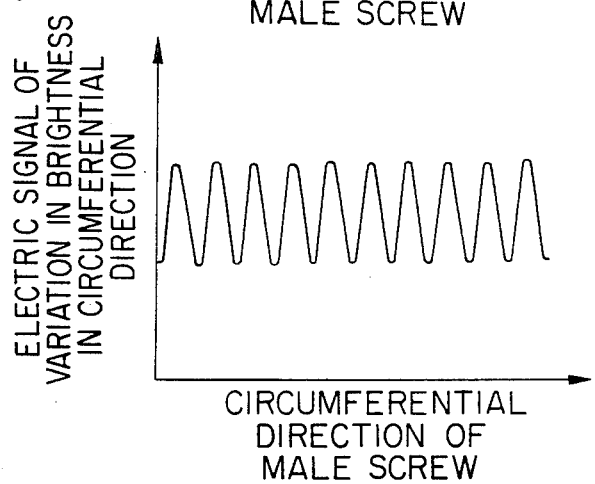

Now, the process of detection of a flaw on the threads 2 of the male screw 1 as mentioned above in the flaw-detecting means of the flaw-determining mechanism 6 is explained further in detail with reference to the drawings. FIGS. 6(A) and 6(A') are descriptive views illustrating, in the form developed in the circumferential direction of the male screw 1, the electric signal values corresponding to the variations in brightness of the male screw 1 in the axial direction thereof, as moving-averaged by the first moving average calculating circuit 10 during the one turn of the male screw 1, FIG. 6(A) covering the case of a male screw 1 having threads 2 with no flaws, and FIG. 6(A'), the case of a male screw 1 having threads 2 with flaws. FIGS. 6(B) and 6(B') are graphs illustrating the electric signal values as determined by the memory 11 corresponding to the variations in brightness of the male screw 1 in the circumferential direction thereof, at the position of the line a—a respectively in FIGS. 6(A) and 6(A'). FIGS. 6(C) and 6(C') are graphs illustrating the electric signal values determined by moving-averaging ,the electric signal values in the circumferential direction of the male screw 1 as respectively shown in FIGS. 6(B) and 6(B'), by means of the second moving average calculating circuit 12. FIGS. 6(D) and 6(D') are graphs illustrating the values of differences between the electric signal values in the circumferential direction of the male screw 1 before the moving-averaging as respectively shown in FIGS. 6(B) and 6(B'), on one hand, and the electric signal values in the circumferential direction of the male screw 1 after the moving-averaging as respectively shown in FIGS. 6(C) and 6(C'), on the other hand, as determined by the difference calculating circuit 13.

The range of variations in the electric signal values corresponding to the variations in brightness of the male screw 1 having the threads 2 with no flaws in the circumferential direction thereof, determined by the memory 11, as shown in FIG. 6(A), is very small as shown in FIG. 6(B). As a result, the values of differences, as calculated by the difference calculating circuit 13, between the electric signal values shown in FIG. 6(B) and the moving-averaged electric signal values shown in FIG. 6(C) are very small as shown in FIG. 6(D). Consequently, the mean square value obtained from the values of differences shown in FIG. 6(D) by the mean square calculating circuit 14 is also very small. Thus, the comparing circuit 15 compares this small mean square value with the previously set reference value, to judge that there is no flaw on the threads 2 of the male screw 1.

On the other hand, the range of variations in the electric signal values corresponding to the variations in brightness of the male screw 1 having the threads 2 with flaws in the circumferential direction thereof, determined by the memory 11, as shown in FIG. 6(A'), is large as shown in FIG. 6(B'). As a result, the values of differences, as calculated by the difference calculating circuit 13, between the electric signal values shown in FIG. 6(B') and the moving-averaged electric signal values shown in FIG. 6(C') are large as shown in FIG. 6(D'). Consequently, the mean square value obtained from the values of differences shown in FIG. 6(D') by the mean square calculating circuit 14 is also large. Thus, the comparing circuit 15 compares this large mean square value with the previously set reference value, to judge that there are flaws on the threads 2 of the male screw 1.

In the above description, detection of the electric signal values corresponding to the variations in brightness of the male screw 1 in the circumferential direction thereof has been carried out at the position shown by the line a—a in FIGS. 6(A) and 6(A'). Detection may however be carried out at a plurality of positions along the axis of the male screw 1, not limiting to a single position. When detecting the electric signal values corresponding to variations in brightness in the circumferential direction at a plurality of positions on the male screw 1, a plurality of the second moving average calculating circuits 12, the difference calculating circuits 13, the mean square calculating circuits 14 and the comparing circuits 15 are provided in response to the number of detecting positions to permit detection of the electric signal values corresponding to the variations in brightness in the circumferential direction of the male screw 1 at each of the plurality of detecting positions.

According to the method and the apparatus of the present invention, as described above, it is possible to ensure rapid detection of flaws such as chattering flaws produced on tops and roots of threads of a male screw, thus providing industrially useful effects.

What is claimed is:

1. A method for detecting a flaw on threads of a male screw, which comprises:

uniformly applying a light onto substantially the entire surface of threads of a male screw in the axial direction thereof and at least part of the surface of said threads of said male screw in the circumferential direction thereof while rotating said male screw at a prescribed circumferential speed around the axis thereof;

continuously measuring, during one turn of said male screw around the axis thereof, electric signal values corresponding to variations in brightness of the surface of said male screw in the axial direction thereof, which are caused by tops, roots and flanks of said threads of said male screw onto which said light is applied;

obtaining an average value of the thus measured electric signal values corresponding to said variations in brightness of said male screw in the axial direction thereof; and comparing the thus obtained average value of said electric signal values with a previously set reference value, to detect a flaw on said threads of said male screw;

characterized by:

fully applying said light onto the tops, the roots and the flanks of said threads of said male screw; and said obtaining step of said average value of said electric signal values comprises:

(1) moving-averaging, during said one turn of said male screw, said electric signal values corresponding to said variations in brightness of said male screw in the axial direction thereof;

(2) continuously determining, during said one turn of said male screw, electric signal values corresponding to variations in brightness of said male screw in the circumferential direction thereof, on the basis of the thus moving-averaged electric signal values corresponding to said variations in brightness of said male screw in the axial direction thereof; and (3) obtaining a mean square value from the thus determined electric signal values corresponding to said variations in brightness of said male screw in the circumferential direction thereof, thereby using the thus obtained mean square value of said electric signal values as said average value of said electric signal values to compare said mean square value of said electric signal values with said previously set reference value to detect a flaw on said threads of said male screw.

2. The method as claimed in claim 1, wherein:

said obtaining step of said mean square value of said electric signal values comprises:

(1) moving-averaging, during said one turn of said male screw, said electric signal values corresponding to said variations in brightness of said male screw in the circumferential direction thereof;

(2) determining, during said one turn of said male screw, values of differences between the thus moving-averaged electric signal values corresponding to said variations in brightness of said screw male in the circumferential direction thereof, on one hand, and said electric signal values before said moving-averaging corresponding to said variations in brightness of said male screw in the circumferential direction thereof, on the other hand; and (3) obtaining said mean square value of said electric signal values from the thus determined values of differences.

3. An apparatus for detecting a flaw on threads of a male screw, which comprises:

a male screw rotating means for rotating a male screw at a prescribed circumferential speed around the axis thereof;

a light source for uniformly applying a light onto substantially the entire surface of threads of said male screw in the axial direction thereof and at least part of the surface of said threads of said male screw in the circumferential direction thereof;

a photoelectric converter for continuously measuring, during one turn of said male screw around the axis thereof, electric signal values corresponding to variations in brightness of the surface of said male screw in the axial direction thereof, which are caused by tops, roots and flanks of said threads of said male screw onto which said light is applied; and a flaw-determining mechanism for comparing an average value of said electric signal values corresponding to said variations in brightness of said male screw in the axial direction thereof, as measured by said photoelectric converter, with a previously set reference values, to detect a flaw on said threads of said male screw, said flaw-determining mechanism comprising a memory for continuously storing, during said one turn of said male screw, said electric signal values corresponding to said variations in brightness of said male screw in the axial direction thereof, as measured by said photoelectric converter; and a flaw-detecting means for obtaining said average value of said electric signal values corresponding to said variations in brightness of said male screw in the axial direction thereof, as continuously stored in said memory during said one turn of said male screw, and for comparing the thus obtained average value of said electric signal values, with said previously set reference value, to detect a flaw on said threads of said male screw;

characterized in that:

said light source (4) is provided at a position from which said light is fully applied onto the tops, the roots and the flanks of said threads (2) of said male screw (1);

said memory (11) of said flaw-determining mechanism (6) includes a means for continuously determining, during said one turn of said male screw (1), electric signal values corresponding to variations in brightness of said male screw (1) in the circumferential direction thereof, on the basis of said electric signal values corresponding to said variations in brightness of said male screw (1) in the axial direction thereof; and said flaw-detecting means of said flaw-determining mechanism (6) comprises:

a first moving average calculating circuit (10) for moving-averaging, during said one turn of said male screw (1), said electric signal values corresponding to said variations in brightness of said male screw (1) in the axial direction thereof, as measured by said photoelectric converter (5), the thus moving-averaged electric signal values being entered into said memory (11);

a second moving average calculating circuit (12) for moving-averaging, during said one turn of said male screw (1), said electric signal values corresponding to said variations in brightness of said male screw (1) in the circumferential direction thereof, as determined by said memory (11);

a difference calculating circuit (13) for calculating, during said one turn of said male screw (1), values of differences between said electric signal values corresponding to said variations in brightness of said male screw (1) in the circumferential direction thereof, as moving-averaged by said second moving average calculating circuit (12), on one hand, and said electric signal values before said moving-averaging corresponding to said variations in brightness of said male screw (1) in the circumferential direction thereof, as determined by said memory (11), on the other hand;

a mean square calculating circuit (14) for obtaining a mean square value of said electric signal values as said average value of said electric signal values, from said values of differences as calculated by said difference calculating circuit (13); and a comparing circuit (15) for comparing said mean square value of said electric signal values obtained by said mean square calculating circuit (14) with said previously set reference value.

4. The apparatus as claimed in claim 3, wherein:

said light source (4) is provided at a position that the optical axis thereof ($l_2$) intersects the axis ($l_1$) of said male screw (1) at substantially right angles; and said photoelectric converter (5) is provided near said light source (4) at a position that the optical axis ($l_3$) of said photoelectric converter (5) intersects the axis ($l_1$) of said male screw (1) substantially at right angles.

* * * * *